United States Patent [19]

Doeleman

[11] 4,055,797
[45] Oct. 25, 1977

[54] ELECTROLYTIC CONDUCTANCE METER

[75] Inventor: Henry Doeleman, Glendora, Calif.

[73] Assignee: Devon Products, Inc., Los Angeles, Calif.

[21] Appl. No.: 683,182

[22] Filed: May 4, 1976

[51] Int. Cl.² .......................................... G01N 27/42
[52] U.S. Cl. ................................. 324/30 R; 324/72.5
[58] Field of Search ................. 324/30 R, 30 B, 72.5; 204/195 R

[56] References Cited

U.S. PATENT DOCUMENTS

| 3,605,010 | 9/1971 | Folus | 324/30 B |
| 3,806,797 | 3/1974 | Harvey | 324/30 R |
| 3,938,035 | 2/1976 | Fletcher | 324/30 B |

Primary Examiner—M. Tokar
Attorney, Agent, or Firm—John T. Matlago

[57] ABSTRACT

A meter is provided for measuring the total parts per million dissolved solids in an electrolytic solution. The sensor for the meter is located on an upright probe on the face of a mount which is rotatably attached to the casing of the meter. Such a construction enables the sensor to be immersed directly into a batch of the solution while the casing is maintained in an upright position to enable the scale on the upper surface thereof to be viewed by the operator. In addition, a recessed circular opening is provided on the face of the mount about the upright probe to enable the threaded ends of sample bottles to be attached thereto.

6 Claims, 9 Drawing Figures

U.S. Patent  October 25, 1977  Sheet 1 of 2  4,055,797
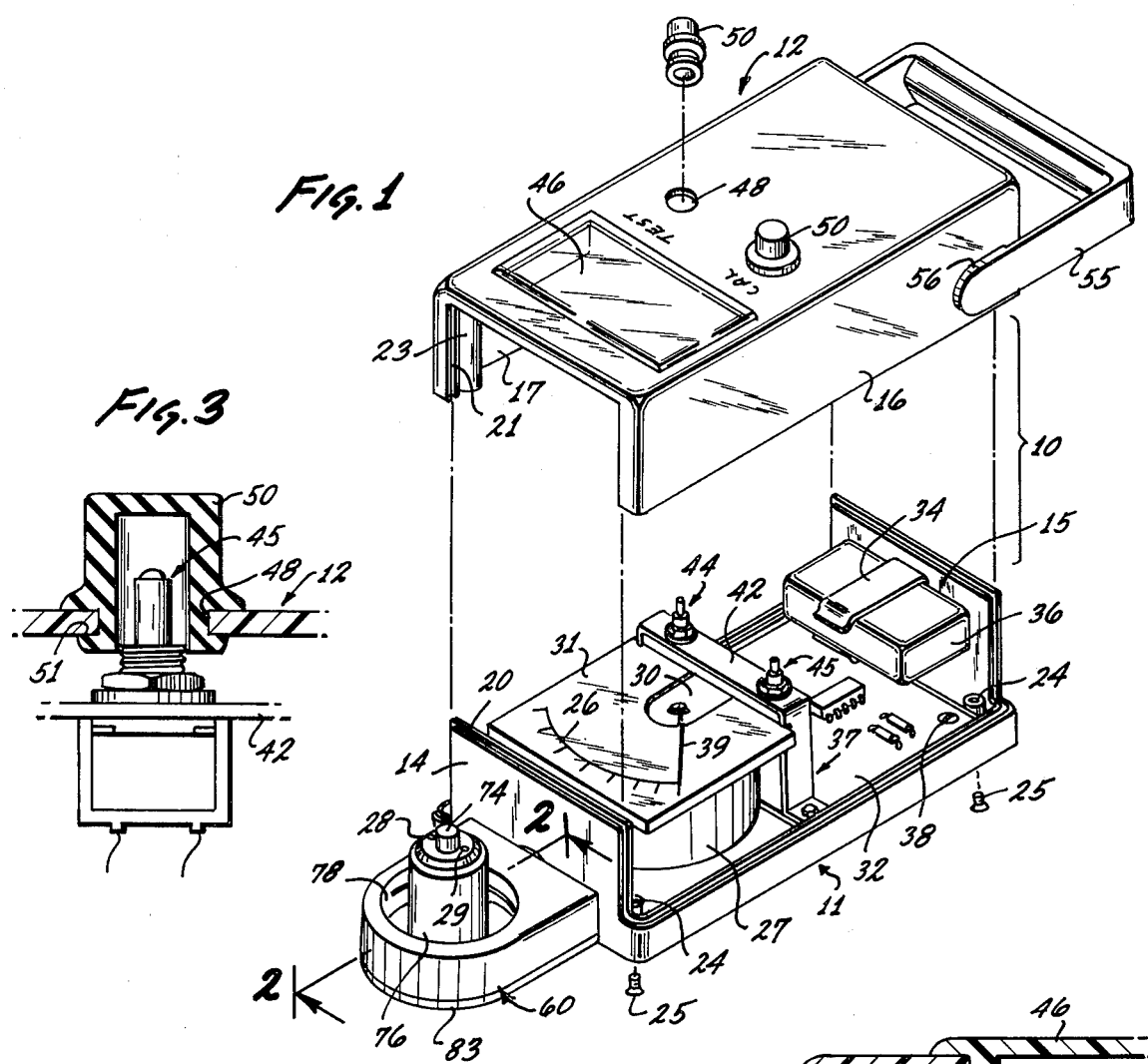
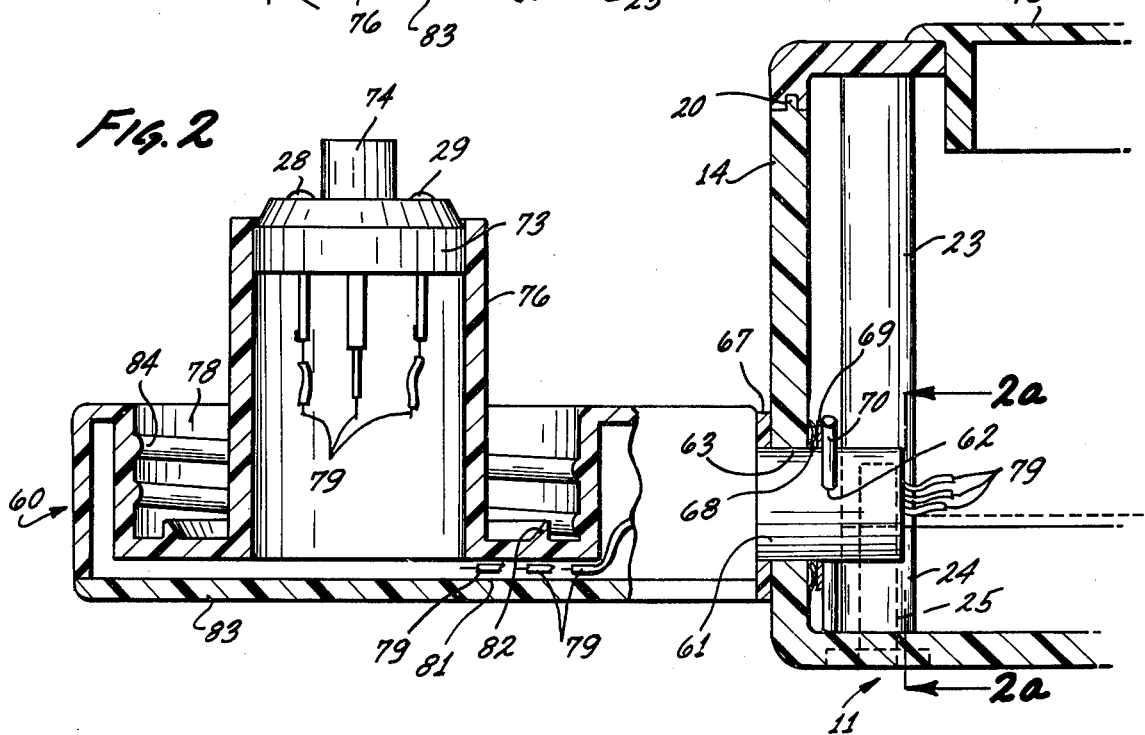

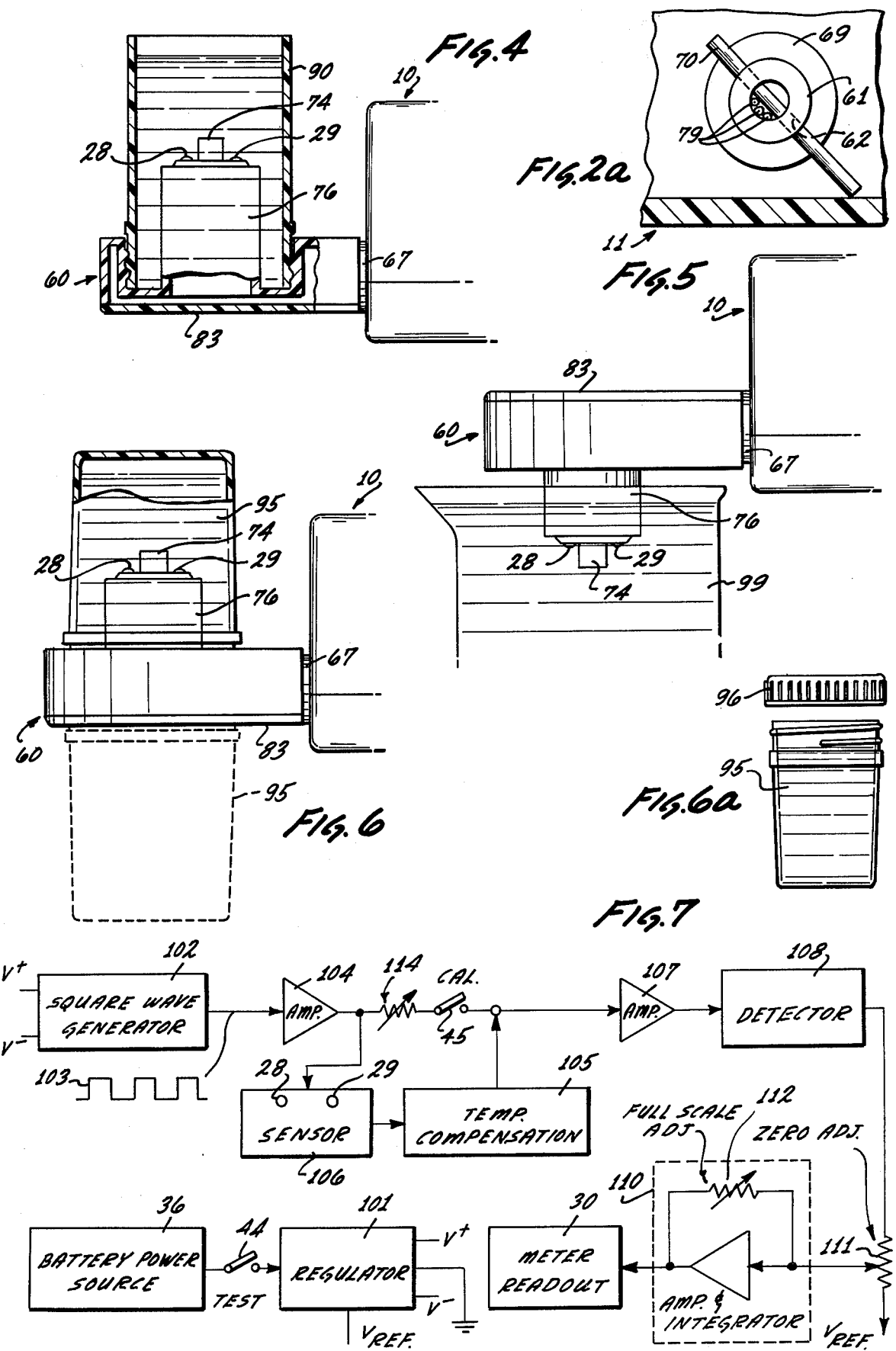

ELECTROLYTIC CONDUCTANCE METER

This invention relates to an electrolytic conductance meter and more particularly to a novel structure for such a meter which enhances its utility.

It is highly desirable to measure the dissolved solids in parts per million in a solution. As an example, such meters are used to determine the degree of the purity of water as needed for industrial purposes. As a further example, such meters are used by hemodialysis patients and medical technicians in testing dialysate solutions for verifying if the prescribed concentration of total ionized salts are present therein.

A portable meter of this type is conventionally constructed with an open well fixed to its casing. A pair of spaced electrodes which form the sensor of an electrical circuit is located on an upright pedestal located with the well. When the well is filled with a sample of the electrolytic solution to be tested, the closing of the electrical circuit by the depressing of a switch on the casing causes current to conduct across the electrodes depending on the total dissolved solids in the solution. This conductance can be displayed as a parts per million reading on a scale that is viewed from the top of the casing.

A difficulty in using such conventional meters arises when it is desired to check the conductance of an electrolytic solution in other ways such as by directly dipping the electrodes into a larger container such as a reservoir containing a batch of the solution. Thus, in order to submerge the upright electrodes fixed relative to the meter casing into the reservoir, it is necessary to turn over the casing. This makes it very inconvenient; if not impossible for the operator to read the meter scale which is now facing downwardly.

Accordingly, one of the objects of the present invention is to provide a novel structure for a portable electrolytic conductance meter.

Another object of the present invention is to provide for the rotatable mounting of a pair of spaced electrodes on the casing of a conductance meter which permits the operator to position the mount relative to the casing to enable the testing to be performed in a manner best suited to his needs.

Another object of the present invention is to provide an electrode mount for an electrolytic conductance meter which is rotatable relative to the casing to enable the electrodes to be immersed directly downwardly into a reservoir containing a large quantity of the solution to be tested while the casing remains upright to facilitate viewing of the meter scale thereon.

Another object of the invention is to provide a portable mount with a threaded recessed circular opening about its upwardly extending electrode pedestal which is adapted to engage the threaded mouth end of a sample bottle filled with solution to be tested.

With these and other objects in view, the invention consists in the construction, arrangement and combination of the various parts of the device whereby the objects contemplated are attained as hereinafter set forth, pointed out in the appended claims and illustrated in the accompanying drawings.

Referring to the drawings:

FIG. 1 shows a perspective view of the meter of the present invention with the cover of the casing exploded from the body thereof;

FIG. 2 is a vertical sectional view taken along line 2—2 of FIG. 1;

FIG. 2a is a view taken along line 2a-2a of FIG. 2;

FIG. 3 is a sectional view showing the relation of the rubber cap to a microswitch when the cover is assembled on the base;

FIG. 4 is a view showing the mount for the electrodes in its upright position with a sample well threadable engaged in position thereon;

FIG. 5 is a view showing the mount for the electrodes inverted to facilitate the immersion of the electrodes into a reservoir of the solution being tested;

FIG. 6 is a view showing the mount rotated into its upright position with the mouth of a bottle containing a sample solution threadable engaged thereon;

FIG. 6a is a perspective view of a bottle of sample solution with its cap removed from the threaded mouth thereof; and FIG. 7 is a block diagram of the electrical circuit for the meter.

Referring to the drawings, the meter of the present invention includes a molded casing 10 comprising a base 11 and a cover 12. The base 11 is formed with rectangularly shaped front and rear end walls 14 and 15, with the sides of the base being open. The cover 12 is formed with rectangularly shaped sidewalls 16 and 17, with the front and rear ends of the cover being open. A projection 20 is formed along the edges of the periphery of the base including the vertical edges of the front and rear end walls 14 and 15 thereof and a groove 21 is formed along the edges of the periphery of the cover 12 including the vertical edges of the sidewalls 16 and 17 thereof. With such a construction, the peripheral edges of the cover 12 and base 11 can be mated to provide a moisture proof fit. In addition, to hold the cover to the base, posts 23 provided on the inner four corners of the cover 12 are aligned with bosses 24 provided on the four inner corners of the base 11 to receive corner fastener screws 25.

Mounted on the front portion of the base 11 is a cylindrical housing 27 enclosing a meter readout movement 30. The housing 27 has a top plate 31 with a meter scale 26 thereon past which the pointer 39 sweeps to indicate the reading of the meter. A printed circuit board 32 with electrical components mounted thereon is attached to the bottom rear portion of the base 11 by screws 38. A clip 34 for a battery 36 is mounted on the rear wall 15 of the base 11. A bracket 37 has its legs attached to the base 11. Mounted on the top cross member 42 of the bracket are a "Test" microswitch 44 and a "Calibrate" microswitch 45.

The front portion of cover 12 is provided with a clear window 46 which is disposed above the scale 26 on the housing. Centrally provided in the cover 12 are a pair of openings 48 which are disposed above the microswitches 44 and 45 attached to the bracket 37. Each of the openings 48 is provided with a rubber cap 50 which has a groove 51 formed about the lower end thereof that fits about the periphery of the opening. A U shaped plastic handle 55 has bosses 56 formed on the inner sides of its legs which are rotatably mounted in openings on the sidewalls 16 and 17 of the cover.

Disposed on the front wall 14 of the body 11 of the casing is a mount 60 having an integrally formed cylindrical hollow hub 61 laterally extending from the end thereof. The hub 61 on the mount has a close rotatable fit in an opening 63 provided on the front wall 14 of the casing. A nylon washer 67 is provided between the end surface of the mount 60 and the front wall 14. A tapered pin 70 is fitted in an opening 62 extending along a diameter near the end of the hub. The pin 70 is spaced from the inner surface of the front wall 14 by a spring washer 68 and a flat washer 69 and thus provides for resiliently holding the mount 60 in position adjacent the inner wall 14 of the casing. The pin 70 extends crosswise beyond the periphery of the hub such that its lower end contacts the bottom of the base 11 (FIG. 2a) and serves to stop the mount 60, upon being rotated to its upright position, such that it is level with the base.

The sensor for the meter comprises a pair of spaced electrodes 28 and 29 cast in a plastic cylindrical unit 73. The unit 73 is provided with a central projection 74 which encloses a thermistor (not shown). The cylindrical plastic unit 73 is cemented in position on the upper end of a tubular electrode pedestal or probe 76 which forms an integral part of the mount 60 and centrally extends out of a circular recessed opening 78 formed on the face of the mount. Three electrical conductors 79 each having one end thereof connected to the elctrodes 28 and 29 and the thermistor extend down into the interior of the electrode pedestal 76 and through a channel opening 81 on the bottom of the mount and the hollow hub 61 on the end thereof to connect to the electrical circuit board 32. The mount 60 is provided with a plastic bottom 83 which can be cemented in position.

The circumferential sidewall 84 of the recessed circular opening 78 on the mount surrounding the electrode pedestal 76 is formed with threads. A circular bead 82 is formed on the bottom of the recess just inwardly of the sidewall 84 thereof. Such a construction enables the threaded end of a tubular well 90 or bottle 95 to engage the threaded wall of the recessed circular opening with the circular edge of the well or bottle seated against the bead 82 to form a water tight seal on the bottom of the mount.

A block diagram of the electrical circuit provided for operating the electrolytic conductance meter of the present invention is shown in FIG. 7. The battery 36 is connected through the "Test" microswitch 44 to a regulator 101 which provides a plus voltage V+ and a minus voltage V− relative to ground. These voltage outputs when applied on square wave generator 102 provide a regulated square wave 103 which is amplified in amplifier 104 and applied across the sensor 106 formed by electrodes 28 and 29 on the electrode pedestal 76 of the mount 60. The output signal of the sensor 106 passes through a temperature compensating circuit 105, which includes the thermistor enclosed in the central projection 74 of the unit 73, and through amplifer 107 to detector 100. This signal is then fed into an integrator and amplifier circuit 110 which converts the d.c. signal square wave to a d.c. current signal for feeding to the meter readout movement 30.

During initial setup of the meter, the setting of pointer 39 relative to the scale 26 is adjusted by use of the "zero adjust" potentiometer 111 and the "full scale adjust" potentiometer 112. Thus in order to properly read the scale 26 which is set to read from a minimum value to a maximum value, the "zero adjust" potentiometer 111 is adjusted so that the pointer 39 will properly read these values when the electrode pedestal 76 is placed in a sample solution having these standard readings. To further assist in the scale settings the "full scale adjust" potentiometer 112 is adjusted to provide for the pointer 39 having an overall arcuate movement corresponding to the range provided for the scale 26.

As a further step in the setup, the setting of the potentiometer 114 is adjusted to cause the pointer 39 to read at the midpoint of the scale 26 which the "Calibrate" microswitch 45 on the cover is depressed to bring a resistor of standard value into the circuit which shunts the sensor circuit. During the use of the meter, a calibration check thereof can be made at any time by depressing both the "Calibrate" and the "Test" microswitches 44 and 45 to determine if the pointer 39 properly reads the midpoint of the scale 26. This procedure not only assures that the battery 36 is at full capacity but also that the remaining circuit components on the printed circuit board are properly functioning.

In view of the above, it should now be clear that the providing of a meter with a casing 10 having a rotatable mount 60 attached thereto on whose upper face the upright electrode pedestal 76 is supported, together with the providing of threads on the sidewall 84 of the recessed circular opening 78 surrounding the electrode pedestal 76 is highly advantageous since it provides for flexibility in the manner in which the meter can be used for testing solutions.

Thus, as shown in FIG. 4, a well 90 in the form of a tube threaded at one end thereof can be positioned to surround the electrode pedestal 76 and seated with its threaded end engaged on the threaded recessed opening 78 of the mount 60. When so assembled with the face of the mount in its upright position relative to the casing 10, a sample of a batch solution of an electrolyte to be tested by the meter can be poured into the well 90 so as to cover the electrodes 28 and 29. The pressing of the rubber cap 50 above the "Test" microswitch 44 closes the connection of the battery 36 to the electrical circuit and causes the pointer 39 of the meter movement to indicate the total parts per million of solids in the electrolyte.

As an alternate method of use, as illustrated in FIG. 5, the mount 60 can be rotated on its hub 61 relative to the casing 10 with its electrode pedestal 76 extending downwardly so that it can be directly dipped into the batch solution being held in a large beaker 99, for example. When the electrodes 28 and 29 are so immersed, the casing 10 is properly oriented so that the pointer 39 as viewed through the window 46 of the cover can be easily read by the operator.

As a third alternative method of use, as illustrated in FIG. 6, a standard sample bottle 95 (FIG. 6a) having threads on the mouth end thereof for a threaded cap 96 may be used to perform the test. Thus with the mount 60 rotated to its inverted position, the water tight cap 96 can be removed from the mouth end of the bottle 95 filled with a sample solution, and the mouth end of the bottle can then be screwed into the threaded recessed opening 78 of the mount 60 so as to have a liquid tight fit thereon. The attachment of the bottle 95 to the inverted mount 60 is illustrated by dashed lines in FIG. 6. The mount 60 with the bottle 95 of solution engaged thereon can then be rotated back to its upright position relative to the casing 10 so that the electrode pedestal 76 is covered with the solution. Since the casing is in its upright position, the scale is in position for easy viewing by the operator for reading.

While the invention shown and described herein has been well adapted to fulfill the objects and advantages previously mentioned as desirable, it is to be understood that the invention is not limited to the specific features shown and described but that the means and configuration herein disclosed are susceptable of modification in form, proportion and arrangement of parts without departing from the principle involved or sacrificing any of its advantages and the invention is therefor claimed in embodiments of various forms all coming within the scope of the claims which follow.

I claim:

1. In a portable meter for measuring the conductance of an electrolytic solution, the combination comprising:
   a casing;
   a meter movement in said casing including a pointer movable relative to a scale viewed through a window on the upper surface of said casing;
   an electrical circuit in said casing for controlling the movement of said pointer; and
   a mount having a hub rotatably mounted on the end of said casing, said mount including a recessed threaded circular opening on the face thereof with a probe arising from the center thereof having a pair of spaced electrodes connected to the electrical circuit, and said mount being rotatable on its hub such that the probe on the face thereof is in an upright position or a downward position relative to the scale as viewed from the upper surface of said casing.

2. The invention in accordance with claim 1 including a tubular well having one end thereof threaded for engagement on the recessed threaded circular opening on the face of said mount.

3. The invention in accordance with claim 1 including a sample bottle having a mouth end threaded for engagement on the recessed threaded circular opening on the face of said mount.

4. The invention in accordance with claim 1 including means on said hub for limiting the rotation of said mount when it is rotated to an upright position such that its face is parallel with the upper surface of said casing.

5. The invention in accordance with claim 4 wherein said means includes a cross-pin on said hub whose end extends to contact the casing to thereby limit the rotation of said mount.

6. In a portable meter for measuring the conductance of an electrolytic solution, the combination comprising:
   a casing;
   a meter movement in said casing including a pointer movable relative to a scale viewed through a window on the upper surface of said casing;
   an electrical circuit in said casing for controlling the movement of said pointer; and
   a mount having a hub rotatably mounted on the end of said casing, said mount including a recessed threaded circular opening on the face thereof with a probe arising from the center thereof having a pair of spaced electrodes connected to the electrical circuit;
   said electrical circuit including a battery, a standard resistance, and a pair of microswitches, said microswitches extending through openings in said cover, one of said microswitches providing for connecting said battery to energize said electrical circuit and the other of said microswitches providing for shunting said standard resistance across the pair of spaced electrodes in said electrical circuit whereby when said microswitches are simultaneously depressed said electrical circuit provides for moving said pointer to a predetermined point of said scale; and
   said mount being rotatable on its hub such that the probe on the face thereof is in an upright position or a downward position relative to the scale as viewed from the upper surface of said casing.

* * * * *